United States Patent [19]
Schapira et al.

[11] Patent Number: 5,349,874
[45] Date of Patent: Sep. 27, 1994

[54] METHOD FOR MICROBIOLOGICAL MONITORING

[75] Inventors: Simon F. D. Schapira, Aberdeen, Scotland; Robin W. Eycott; William P. Richardson, both of Bucks, England; Jim S. Robinson, Surrey, England

[73] Assignee: Houseman Limited, United Kingdom

[21] Appl. No.: 777,158

[22] Filed: Oct. 16, 1991

Related U.S. Application Data

[63] Continuation-in-part of Ser. No. 306,937, Feb. 6, 1989, abandoned.

[30] Foreign Application Priority Data

Feb. 4, 1988 [GB] United Kingdom ............... 8802473

[51] Int. Cl.⁵ .................... G01N 17/00; G01N 33/48
[52] U.S. Cl. ............................................. 73/864; 73/86
[58] Field of Search ................ 73/86, 864, 863.85

[56] References Cited

U.S. PATENT DOCUMENTS

| | | | |
|---|---|---|---|
| 2,928,726 | 3/1960 | Oberly | 422/53 |
| 3,174,332 | 3/1965 | Echler, Jr. et al. | 73/86 |
| 4,002,057 | 1/1977 | Kannapell et al. | 73/61.2 |
| 4,043,178 | 8/1977 | Winslow, Jr. | 422/53 |
| 4,044,605 | 8/1977 | Bratthäll | 73/61.2 |
| 4,226,693 | 10/1980 | Maes | 73/86 |
| 4,275,592 | 6/1981 | Atwood et al. | 73/86 |
| 4,309,506 | 1/1982 | Squires | 435/291 |
| 4,506,540 | 3/1985 | Marsh | 422/53 |
| 4,537,071 | 8/1985 | Waterman | 73/432 R |
| 4,631,961 | 12/1986 | Yohe et al. | 73/86 |
| 4,631,967 | 12/1986 | Welker | 73/861.25 |
| 4,686,854 | 8/1987 | Herman | 73/86 |
| 4,688,638 | 8/1987 | Williams | 73/86 |
| 4,697,465 | 10/1987 | Evans et al. | 73/86 |
| 4,841,787 | 6/1989 | Waterman | 73/866.5 |
| 4,945,758 | 8/1990 | Carpenter | 73/86 |
| 5,049,492 | 9/1991 | Saver et al. | 73/863.85 |

OTHER PUBLICATIONS

McCoy et al., "Observations of Fouling Biofilm Formation", *Can. J. Microbiol.* 27: 910–917, May 29, 1981.

*Primary Examiner*—Hezron E. Williams
*Assistant Examiner*—George Dombroske
*Attorney, Agent, or Firm*—Ostrolenk, Faber, Gerb & Soffen

[57] ABSTRACT

Disclosed is a method for monitoring biofilm formation which comprises incorporating in an aquatic system, a sampler apparatus comprising a duct 1 having a port 5 in which is retained a stud 17 having a test surface 19 which lies flush with the wall of the duct. The invention can also be used to detect Legionellae bacteria.

28 Claims, 1 Drawing Sheet

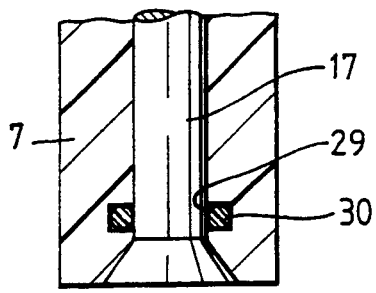
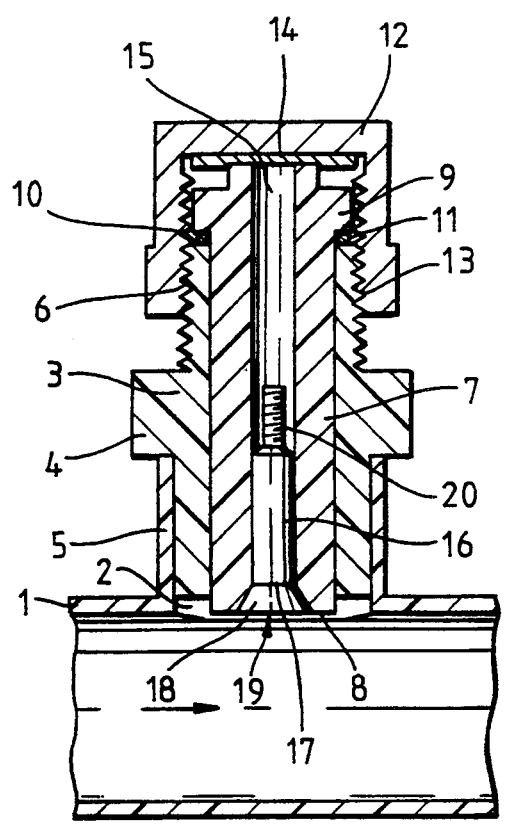
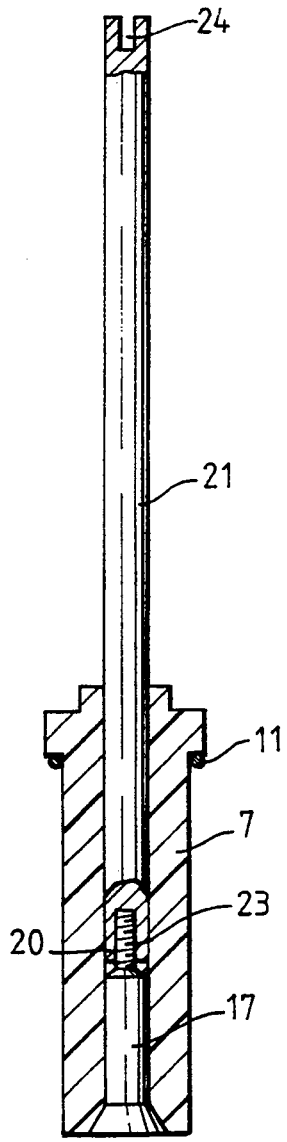
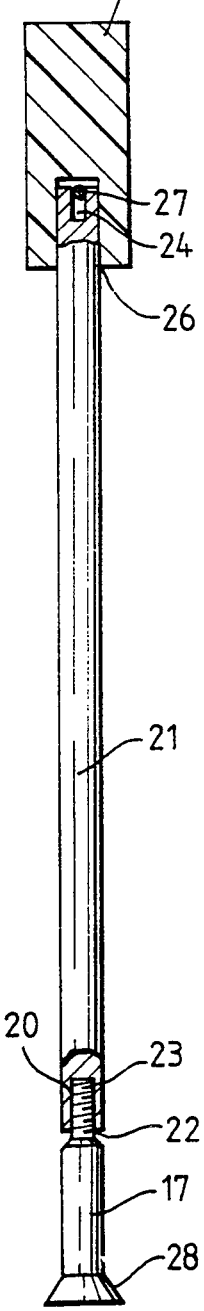

METHOD FOR MICROBIOLOGICAL MONITORING

This is a continuation-in-part of application Ser. No. 07/306,937, filed Feb. 2, 1989 and now abandoned.

BACKGROUND OF THE INVENTION

1. Field of the Invention

The present invention relates to method for monitoring the buildup of films of microorganisms on surfaces in aquatic systems, such as in heat exchangers, waste water transport and secondary oil recovery, particularly in recirculating water systems such as in cooling systems. In particular the invention relates to a method which is more easily carried out than known methods of this type. The invention also relates to the detection and monitoring of pathogenic bacteria in association with such films.

2. Brief Description of the Prior Art

In all industrial, domestic and medical aquatic systems there are many factors which can create problems by reducing the efficiency of the process concerned or by creating toxicity problems. Water used in most of these systems will usually contain some form of living microorganisms which under the conditions in the systems concerned can multiply and cause a number of problems. Initially the microbes are introduced suspended in the water. These so-called planktonic microorganisms are relatively easy to detect and monitor and also to kill using conventional biocides. Although they can cause problems, for instance if the microorganisms are pathogenic, in general they do not significantly affect the overall efficiency of the system.

The planktonic microorganisms can however become adherent to internal surfaces in the system when they are known as "sessile". Sessile bacteria can proliferate and some bacteria generate so called slime composed mainly of polysaccharide and form a film upon the surface. These films have recently been recognised as contributing to inefficiencies in the systems for various reasons. For instance the films will reduce efficiency of conductive heat transfer through the surfaces and, since they are highly elastic, increase fluid frictional resistance at the surface dramatically. Furthermore some types of bacteria produce compounds which may be environmentally hazardous or may lead to corrosion of metal in the surface to which the film is attached. Sulphate reducing bacteria or SRB's in particular can give rise to serious corrosion of metal surfaces. Of the environmentally hazardous bacteria, Legionella bacteria are known to occur widely in natural and man-made aqueous systems. L. pneumophila are the most common cause of Legionella related diseases in man, and also appears to be the most common species in a man-made environment. The pathogenic nature of Legionella bacteria means that their detection and monitoring is particularly important.

Bacteria in biofilms are in general found to be difficult to get rid of, partly because chemical biocides must penetrate the slime before they reach the target microorganisms deep within the films. Because of the problems that biofilms can create, it is important to be able to detect the appearance of the biofilms in order to know when a dose of a suitable biocide is necessary to prevent development of films and to get rid of existing films, as well as to be able to detect the removal of such films after treatment with such a biocide. Since films which are so thin as to be invisible to the naked eye can cause severe problems it is desirable to be able to detect films by other means. The absence of significant numbers of planktonic bacteria does not necessarily indicate the absence of sessile bacteria. For example, studies have shown that drinking water can be colonised with microorganisms despite treatment of the source water to standards set by the EEC and WHO guidelines. It has been suggested ("A Continuous Culture Biofilm Model for the study of Medical and Industrial Corrosion", Keevil et al) that the transient appearance of pathogens such as Legionella in these waters might indicate that biofilms provide protected micro environments for microbial survival.

In addition, Lechevallier et al (1988) reported that the concentration X time product required to kill 99% of the heterotrophic bacteria in a biofilm with HOCl was 150–3000×greater than for the same organisms freely suspended in the water.

With regard to Legionella bacteria, it has been recorded subsequent to the priority date of this application in Journal of Applied Bacteriology Symposium Supplement 1991, 70, 121S–129S (Lee and West) that the control measures for the prevention of Legionella bacteria in aquatic systems must be targeted at the prevention of biofilm development.

Thus, the importance of the provision of an effective method for monitoring the presence and development of biofilm in aquatic systems has been confirmed. In the case of pathogens such as Legionella bacteria, the link between transient appearances of pathogenic planktonic bacteria and biofilms emphasises the particular importance of biofilm detection and monitoring.

One type of device for monitoring biofilm buildup is described in the Canadian Journal of Microbiology (1981), volume 27, pages 910 to 917, in which McCoy et al describe the use of a so-called Robbins device which comprises a tube through which water in a recycling circuit can flow. The tube has a plurality of ports in its walls, each being provided with a stud having a biofoulable surface and being capable of being retained in the port in fixed relationship with respect to the tube so that the biofoulable surface forms part of the internal surface of the tube. The studs may be removed from the ports after a desired time interval and the test surfaces by microscopy of the surfaces analysed for the growth of microorganisms or by removal of the microorganisms from the surfaces and subsequent estimation of the degree of growth. The number of microorganisms can be estimated for instance by physical or chemical means, e.g. by detection of bacterial ATP or by further culturing the microorganisms and analysing the products.

One problem with conventional Robbins devices is that it is difficult to remove the studs from their retaining means for analysis of the biofilm and, having removed the stud, it is difficult to handle such a small component aseptically to avoid cross-contamination.

Ruseska et al in Oil and Gas Journal, March 8th 1982 describe the removal of biofilm bacteria from the test surfaces of a Robbins device by scraping with a sterile scalpel. It is difficult to remove all traces of the film from the surface using a scalpel. In "Developments in Industrial Biology" (1982) chapter 53, McCoy and Costerton describe the removal of biofilm from studs by dropping the entire stud into a test tube containing water and metallic tumbling abrasive. The tube is vortexed for two minutes to abrade the film from the surface. A problem with the latter form of removal of biofilm is that film from other areas of the stud is also removed into the same water. This can lead to erroneous results since bacteria growing on such surfaces do not necessarily simulate growth on the internal surfaces of the rest of the recirculating water system, the conditions of flow and other apsects of their environment possibly being significantly different. It is practically impossible to prevent growth occurring on such surfaces but it would be desirable to be able to sterilise such surfaces without affecting the film on the test surface before its analysis.

Accordingly all the present forms of apparatus are difficult to handle or give results that are inevitably inaccurate, or both.

In U.S. Pat. No. 3174332 an apparatus described as a Test Coupon Positioner is described which tests the effects of coal slurries pumped under pressure on metallic "coupons". The device allows coupons to be positioned in the bulk fluid flow within a pipeline and to be removed after predetermined periods for investigation of any corrosion or erosion of the coupon. The coupons may be removed by use of a removal member which has mounting means for connection with the coupon positioner.

However, the provision of a coupon in the bulk flow of the liquid would be an ineffective method of detecting and monitoring biofilm formation on internal surfaces of the aquatic system because the liquid flow characteristics, past the surface, affect biofilm build-up. Therefore, since bulk flow is not the same as liquid flow characteristics past the internal surfaces of the system, such a coupon would not be effective as a biofilm monitor for internal surfaces as it is not representative of such surfaces.

SUMMARY OF THE INVENTION

According to the present invention there is provided a method for monitoring biofilm formation on surfaces in aquatic systems comprising incorporating in the aquatic system a sampler apparatus comprising a duct which forms a channel for a flow of water and has at least one port in its wall, a stud having a test surface to be exposed to the aquatic system and retaining means for retaining the stud in the port in fixed relationship with respect to the tube so that the test surface is flush with the wall and is exposed to water in the channel and retaining the stud in the sampler apparatus for an interval for testing, removing the stud from the port using a stud removal member, the stud and stud removal member having mutual mounting means suitable to rigidly mount the stud on the stud removal member for removal from the apparatus, and collecting and analysing the bacteria from the test surface of the stud.

The invention also includes a method for monitoring the presence of Legionella bacteria in sessile bacteria in an aquatic system comprising incorporating in the aquatic system a sampler apparatus comprising a duct which forms a channel for a flow of water and has at least one port in its wall, a stud having a test surface to be exposed to the aquatic system and retaining means for retaining the stud in the port in fixed relationship with respect to the tube so that the test surface is flush with the wall and is exposed to water in the channel and retaining the stud in the sampler apparatus for an interval for testing, removing the stud from the port using a stud removal member, the stud and stud removal member having mutual mounting means suitable to rigidly mount the stud on the stud removal member for removal from the apparatus, and collecting and analysing the bacteria from the test surface of the stud for the presence of Legionella bacteria.

The interval for testing is the length of time during which the stud test surface is exposed to the aquatic system prior to removal from the sampler apparatus. Thus, the interval may be any length of time during which bacterial build-up may have occurred on the internal surfaces of the aquatic system. The interval may be any desired length of time but, for example, in a cooling system, tests could be carried out on a weekly basis and a first stud could therefore be removed after 7 days, a second stud after 14 consecutive days etc. Alternatively, studs could be removed after 7 days, then after bacteria collection, replaced for a further 7 days. Depending upon the dosages of biocide, testing could be carried out on a more or less frequent basis. In practice, monthly testing will often be used and testing even less frequently may be adequate.

The duct of the sampler apparatus used according to the present invention is usually a tube although it could be another type of duct through which water can flow and in the wall of which the retaining means can retain the stud.

This method of detection and monitoring any biofilm formation is of particular use for monitoring the growth of sessile microorganisms on pipe and other duct walls in aquatic systems and so the stud is capable of being retained so that its test surface is flush with the duct wall. In such a position the test surface lies in the laminar flow or boundary layer region in the pipe and this is critical to effective detection and monitoring according to the present invention. The test surface is therefore designed to mimic the internal geometry of for example a part of a tube or length of fluid distribution pipe work. This ensures that the test surface will on average, have the same type of biofouling build up as any other internal surface part of the system and that it therefore produces a sample of bacteria representative of the bacterial build up on the internal surfaces of the system as a whole.

Generally the sampler comprises a plurality of studs with respective retaining means. Some times the sampler may comprise a single port in the duct and retaining means for retaining a plurality of studs within that port, for instance of the type sold by Caproco Corrosion Prevention Limited for on-line monitoring of circulating water systems. Preferably however the sampler comprises a duct having a plurality of ports each having a respective stud held in position by respective retaining means. This enables various studs to be removed from the sampler after different time intervals, continuously, so that the bacterial build up can be monitored continuously for a system. The duct may be connected in series with the system being monitored or, preferably, it is connected in parallel so that a portion only of the water from the system circulates through it. In such a system in which the duct forms a sidestream the duct may be closed off from the flow by isolating valves at each end of the duct whilst the main circulation through the system continues. The method may then be carried out by examination of the studs may then be examined optionally after disconnection of the entire sampler apparatus from the system.

Preferably, the method can be used as a predictor of growth in the rest of the system. This can be achieved by connecting the duct into the circuit so that the conditions of water flow and temperature through the duct are independently adjustable. The conditions can then be optimised for sessile bacterial growth so that bacterial build up happens earlier in the tube than in the rest of the system.

Preferably the test surface of the stud is substantially flat in order to facilitate the analysis of growth. As in conventional Robbins devices, the stud can have a head with a flat test surface and a stem extending from the opposite side of the head. Preferably the back of the head is conical in shape which aids subsequent sterilisation of the stud and prevention of water migration during use.

In the sampler apparatus the stud is preferably retained in a sleeve as part of the retaining means. The sleeve can be shaped at one end for receiving the stud and minimising water access to surfaces of the stud other than the test surface for instance so that the test surface sits flush with the end of the sleeve. The sleeve may include a seal within its bore for maximising the seal with the stud.

Preferably the mounting means on the stud are such as to allow connection of the stud removal means from the side of the retaining means not facing the flow of water. For instance, a sleeve generally has a bore extending throughout its length through which the stud removal means may be inserted. The sleeve may be held in position in the port of the tube in the apparatus by any suitable cooperating fixing means, for instance so that it is removable from the port whilst still carrying the stud.

The stud removal means is preferably a rod and, if it must pass through a sleeve of the retaining means, has a diameter of the same or smaller than that of the stud stem.

In a further aspect of the invention there is provided a method for removing and handling a stud from the sampler apparatus, the stud having a head with a test surface and a stem leading from the head, the process comprising positioning over the stem of the stud, a bored sleeve, the test surface of the stud remaining exposed and with the stem in a sliding fit in the bore, obtaining a removable rigid rod-shaped stud removal member which is slidable through the sleeve bore, and one end of which has mutually cooperable mounting means with the stud stem, inserting the member into the sleeve bore so that said mutually operable mounting means of one end of the member and the stud stem are brought into cooperation with each other whilst the stud is received in the sleeve, the stud is thereby mounted on the member for handling before and after removal of the sleeve.

The stud may be held in the sleeve simply by friction between the contacting surfaces. Additionally or alternatively the stud may be retained within the sleeve by a pin or pins clips or other like means.

The mounting means via which the stud can be connected to the removal member may include screw threads provided on the stud and the removal member, a bayonet fixing, a push fit or other known alternative connecting means.

The components of the sampler apparatus are made of any suitable materials capable of withstanding corrosion in the system. Usually the stud is of metal, for instance aluminium or steel usually stainless steel. The tube may be made of metal, for instance copper or steel, or, conveniently, of moulded plastics to avoid corrosion and scaling, for instance of moulded acrylonitrile butadiene styrene copolymer (ABS). The sleeve is made of for instance polymers and copolymers of ethylene and propylene, polytetra fluoroethylene or nylon, preferably nylon or polypropylene. The stud removal member can be made of metal or plastics materials, usually metal.

In the preferred method of the invention, to remove the stud from its sleeve, one end of a rod shaped removal member is pushed through the open end of the sleeve and is fixed onto the stud via the mounting means. Then the sleeve is pushed along the length of the member to reveal the stud. The sleeve may be removed entirely or may be retained on the end of the rod distant from the stud as a handle. If the sleeve is removed a separate handle may be provided on the distal end of the stud removal member. The stud can then be treated by whatever means are necessary to collect and analyse the bacteria/biofilm formation, without the stud itself having to be handled. For instance the bacteria may be collected from the stud by swabbing all of the surfaces of the stud other than the test surface using a sterilising composition in order to remove all other traces of bacteria. In the preferred embodiment, when the stud removal member is a rod that is attachable to the stem of a stud, the rod has approximately the same diameter as the stem to provide a continuous surface to aid swabbing. Then the biofilm on the test surface can be further analysed using the stud removal member to manipulate the stud as required. After analysis the stud can be discarded or can be sterilised and reused.

BRIEF DESCRIPTION OF THE DRAWINGS

A preferred method of the present invention is described in more detail with reference to the accompanying drawings, in which:

FIG. 1 is a cross-section through a device in position in the sampler apparatus for monitoring biofilm formation (in the absence of the removal member);

FIG. 2 is a cross-section through an embodiment of the handling apparatus comprising a stud still positioned in a sleeve that has been removed from the port and having a stud removal rod attached to the stud; and FIG. 3 is a cross-section through a stud mounted on a stud removal member having a handle at its distal end:

FIG. 4 is an enlargement of part of FIG. 2 showing extra detail.

DETAILED DESCRIPTION OF THE PREFERRED EMBODIMENT

Referring to FIG. 1, a tube 1 which provides a channel for flow of water as indicated by the arrow, has a port 2 in its wall. The tube is formed of moulded acrylonitrile butadiene styrene copolymer. The port receives a collar 3 of plastics or metal having a flange 4 which bears against the lip 5 around the port. Beyond the flange the collar has screw threads 6 on its external surface.

Within the collar is received a sleeve 7 formed of polypropylene or nylon whose end 8 directed towards the tube is approximately level with the internal surface of the wall of the tube. The sleeve has an external flange 9 at its other end which bears against the end surface 10 of the collar via an 0-ring 11 which provides a watertight seal between the components. The sleeve is held within the collar by means of a screw cap 12 e.g. of metal which fits over the sleeve and has screw threads 13 which co-operate with the external screw threads 6 of the collar. The cap has a gasket 14 which provides a water tight seal between the cap and the open end of the sleeve even when the cap is only hand tightened. Where the monitor is exposed to possible interference, it can be provided with a tamper-proof device to prevent removal of the caps, for instance comprising lockable means.

The sleeve has a central bore 15 of approximately the same internal diameter as the external diameter of the stem 16 of a stud 17 formed of aluminium. The stud has a head 18 with sloping shoulders and a test surface 19 which, when in position in the sampler apparatus, forms part of the boundary of the flow channel through the tube. The bore 15 of the sleeve is shaped at the inner end of the sleeve to receive the shaped stud. As shown in FIG. 4, within the bore there may be an annular depression 29 for receiving an O-ring 30 to form an improved seal between the stud stem and the sleeve to help secure the stud in position and prevent leakage of water into the space behind the stud.

The end of the stud distal from the head has a reduced diameter and is provided with screw threads on its external surface. These form part of the mounting means for attachment to the removal member.

Before connection into a circuit all the components of the sampler apparatus are chemically and physically sterilised. In use water from the circulating system is directed through the tube at a temperature and rate such as to optimise growth conditions so that the device can be used for sessile microorganisms. Microorganisms will attach to surface 19 of the stud, inter alia, and may start to form a film. Usually the apparatus comprises a tube having a plurality of ports with associated collars, sleeves, caps and studs. Development of biofilm may be monitored by removal of one or more studs after a predefined interval after commencement of the monitoring process.

Removal of the stud from the embodiment shown in the drawings can then be carried out with the help of the stud removal member 21 as illustrated in FIGS. 2 and 3 of the drawings. The rod like member has at one end an aperture 22 whose internal surface is provided with screw threads 23 which can co-operate with the screw threads 20 on the stud. The other end of the member is provided with a notch 24. A handle for the member 25 is provided with an opening 26 for receipt of the notched end of the member 21. The opening in the handle has a pin 27 which is capable of co-operating with the notch 24 on the member to retain the handle on the member.

To remove the stud from the apparatus, first of all the flow of liquid through the channel is stopped. Then the screw cap 12 is removed from the collar. This allows removal from the collar of the sleeve 7 still with the stud 17 retained within its bore. In this and subsequent operations care is taken not to allow the test surface 19 to come into contact with other items. The removal member 21 with or without its handle is inserted through the open end of the sleeve and is connected to the stud by means of the mutually co-operating screw threads. When these are completely coupled the handle, if on the rod, is removed to provide the apparatus as illustrated in FIG. 2. As can be seen from the drawing the sleeve may be slid along the length of the member 21 and removed altogether. The handle may then be reapplied to the end of the rod.

The stud is now mounted on the removal member, its rigid mounting enabling it to be handled easily, as illustrated in FIG. 3.

To analyse the deposit on the test surface, it is first preferable to sterilise the other stud surfaces, which are likely to develop some bacterial growth. This may be done by wiping the external surface of the rod and of the stud stem as well as the batch surfaces of the head 28 using alcohol or other sterilising composition. The shoulders on the back of the head are sloping to make satisfactory swabbing of the surfaces easier.

The biofilm on the test surface may be removed from the stud by conventional means, for instance by scraping the film with a scalpel, by ultrasonic irradiation or by the method described by McCoy and Costerton (op.cit.). One advantage of the present invention is that it allows an easier and more effective and consistent way of removing the film. The stud still mounted on the removal member is plunged into a sterile vessel containing sand and water and is moved so as to grind the film from the test surface into the sand. When all the film has been removed the stud may be lifted from the water still attached to the rod. This method of removal of biofilm avoids tumbling of the entire stud in an abrasive and water containing tube. All or a sample of the water may then be analysed by conventional microbiological testing procedures. For instance the number of viable microorganisms in the sample and thus in the film may be estimated and/or identified by culturing methods. The number of bacteria may also be estimated by microscopic methods or by the ATP assay method described by McCoy and Costerton (op cit). Alternatively the film on the test surface of the stud may be analaysed by microscopic techniques, for instance by electron microscopy, fluorescence microscopy or light microscopy.

The method according to the invention enables the apparatus to be used by operators who are relatively unskilled in microbiological techniques for instance by the engineers or chemists normally responsible for running and monitoring the water system.

The example below illustrates use of the method of the invention for monitoring Legionella bacteria in biofilms.

EXAMPLE

Apparatus was assembled to mimic water circulation in a water cooling system. A system was devised incorporating a sampler apparatus as described above comprising 10 ports, each port containing a single stainless steel stud, the surface of which was substantially flush with the internal surface of the apparatus. A water reservoir comprising a 5 l glass vessel was provided and was used to hold the bulk of the recirculating water up to the 3 l level. Cooling water was recirculated by means of a pump, leaving the water reservoir vessel by means of a rubber tube touching the bottom of the vessel and entering by means of a shower head placed inside the lid of the glass vessel which was sealed to be substantially air-tight.

Artificial cooling water, seeded with general cooling water bacteria and *L. pneumophila* SG1 was contained in a 25 l drum. Water from the 25 l drum was continuously pumped into the water reservoir vessel by means of a peristaltic pump and peristaltic tubing. The rate of water entering the main vessel was 3.5 ml/min.

Rubber tubing was placed through the vessel lid until the bottom of tube touched the 3 l water level in the reservoir. Hence, as water was pumped into the vessel and the level rose above 3 l, cooling water was also pumped out through the waste tube. This waste water was pumped into a waste drum containing chlorine release tablets.

No biocide was dosed into the water circulating system.

The retention time in minutes of the water in the main water reservoir vessel was 857 mins (14.3 hours).

After certain specified time intervals (noted in the tables of results), a stud was removed in accordance with the following procedure. The recirculating pump to the sampling apparatus was switched off and the sampler was carefully separated from the system. The cooling water from the entire length of the sampler apparatus was poured into a sample bottle to be used for testing the planktonic Legionella and general planktonic bacteria counts. The required stud/s was then removed by positioning a bored sleeve over the stem of the stud in a sliding fit, placing a rod-shaped stud removal member through the sleeve bore and mounting the end of the stud stem on the end of the stud removal member to remove the bio stud, care being taken not to disturb the biofilm. New studs were securely positioned in each of the empty ports and the sampling apparatus was re-incorporated into the recirculating system.

Meanwhile, all non-filming surfaces of the bio stud and handling apparatus were sterilised by wiping them with a tissue moistened with methylated spirit.

The test surface of the bio stud was gently rinsed with sterile Ringers solution (1/40th strength) to remove planktonic organisms in the water film overlying the biofilm. The sessile bacteria was then removed from the test surface of the bio stud by grinding the stud in 2 g of fine sand and 20 ml of 1/40th strength Ringer solution contained in 30 ml container. The biofilm was then broken up by sealing the container and the mixing the contents vigorously for 30 seconds. The coarse particles of sand were allowed to settle out for approximately 10 seconds and all of the remaining supernatent, approximately 20 ml was removed and placed in a clean sterile centrifuge tube. After 30 min spinning at 4000 rpm to concentrate the organisms, the supernatent was removed and discarded. 2 ml of 1/40th strength Ringer solution (sterile) was added to the resulting pellet and mixed to disperse the contents. $2 \times 0.5$ ml aliquots was injected into sterile 10 ml centrifuge tubes and the remaining 1 ml in the original tube was used for 10 fold dilutions using 1/40th strength Ringer solution up to x $10^2$ dilution.

The $2 \times 0.5$ ml aliquots were treated, one by heat treatment and one by acid treatment. The heat and acid treatments are standard procedures when monitoring Legionella bacteria. The numbers of Legionella bacteria are relatively small compared with the numbers of general bacteria. The heat and acid treatment conditions affect general bacteria but are withstood by Legionella. Thus, these treatments reduce the relative numbers of general bacteria to enable easier identification and analysis of Legionella bacteria present. Prior to heat treatment, a neat concentrate sample comprising 0.1 ml was taken from the 0.5 ml aliquot going to heat treatment, before heat treatment and this 0.1 ml was used to inoculate an untreated plate. Thus, the tube with the neat concentrate for heat treatment at this stage contained 0.4 ml whilst the $10^1$ and $10^2$ dilutions contained 0.5 ml.

For the heat treatment, the tube was placed in a water bed at 50° C. for 30 minutes.

For the acid treatment, 0.5 ml of acid buffer was mixed with the 0.5 ml sample in the tube and the mixture left for 5 mins.

Using the spread plate technique, agar plates were spread with the following aliquots:
untreated and heat treated suspensions 0.1 ml
acid treated suspension 0.2 ml.

The plates were incubated at 37° C. in a humid atmosphere for up to 10 days and bacteria identifications were carried out.

The sensitivity of the test method as above is 20 c.f.u.'s/stud surface or 16 c.f.u.'s/cm$^2$. (The surface area of each stud test surface in this example was 1.2 cm$^2$).

The amounts of planktonic Legionella bacteria and planktonic general bacteria were analysed from the aqueous sample removed from the sampler apparatus.

Analysis for planktonic general bacteria was by the method described in NAMAS (National Measurement Accreditation Service) Microbiology Manual. Analysis for planktonic Legionella bacteria was carried out by concentrating a 200 ml portion of the aqueous sample by centrifugation at 6100 G for 10 mins down to a remaining sample of 2 ml. The 2 ml sample was used in the same way as the 2 ml sample obtained from the biofilm bacteria with Ringers solution. Thus, aliquots were used for heat treatment, acid treatment and dilutions, and agar plates were spread with these samples using the spread plate technique. The plates were incubated as above.

The results are given in Tables 1 and 2 attached.

The results show that the method of the present invention can be used to successfully detect and monitor the presence of biofilm bacteria and in particular, sessile Legionella bacterial. Legionella bacteria were isolated from the test surfaces of the studs taken from each sampling apparatus. Sessile Legionella were isolated at levels up to $10^5$ cfu/cm$^2$. Sessile general bacteria were isolated at levels up to $10^7$ cfu/cm$^2$. As illustrated by the results, the levels of sessile general bacteria were higher than levels of planktonic general bacteria.

Levels of sessile and planktonic Legionella bacteria were almost identical. It appears that maintenance of high planktonic Legionella bacteria levels may encourage increased sessile Legionella numbers.

TABLE 1

| DAYS AFTER STUD INSERTED | RESULTS OF BIOFILM STUDY USING THE 10-PORT LEGIONELLA RIG | | | |
|---|---|---|---|---|
| | PLANKTONIC COUNT (CFU/ML) | | SESSILE COUNT (CFU/CM$^2$) | |
| | LEGIONELLA | GENERAL BACTERIA | LEGIONELLA | GENERAL |
| 38 | $3.76 \times 10^3$ | $1.3 \times 10^5$ | $6.4 \times 10^3$ | $5.1 \times 10^8$ |
| 42 | $3.72 \times 10^3$ | $1.1 \times 10^5$ | $5.76 \times 10^3$ | $4.0 \times 10^6$ |
| 43 | $2.4 \times 10^4$ | $6.0 \times 10^5$ | $3.68 \times 10^4$ | $7.7 \times 10^6$ |
| 41 | $1.0 \times 10^4$ | $3.0 \times 10^5$ | $1.3 \times 10^4$ | $1.2 \times 10^6$ |
| 34 | $1.7 \times 10^4$ | $3.9 \times 10^5$ | $2.4 \times 10^4$ | $2.7 \times 10^6$ |
| 34 | $1.7 \times 10^4$ | $2.5 \times 10^5$ | $2.4 \times 10^4$ | $1.06 \times 10^6$ |
| 34 | $1.6 \times 10^4$ | $9.2 \times 10^4$ | $2.7 \times 10^4$ | $1.06 \times 10^6$ |
| 34 | $1.6 \times 10^4$ | $8.8 \times 10^4$ | $6.4 \times 10^3$ | $4.9 \times 10^6$ |
| 35 | $1.4 \times 10^4$ | $4.3 \times 10^4$ | $8.0 \times 10^4$ | $4.6 \times 10^5$ |
| 35 | $1.6 \times 10^4$ | $9.8 \times 10^4$ | $4.8 \times 10^4$ | $4.0 \times 10^5$ |

TABLE 1-continued

RESULTS OF BIOFILM STUDY USING THE 10-PORT LEGIONELLA RIG

| DAYS AFTER STUD INSERTED | PLANKTONIC COUNT (CFU/ML) | | SESSILE COUNT (CFU/CM$^2$) | |
|---|---|---|---|---|
| | LEGIONELLA | GENERAL BACTERIA | LEGIONELLA | GENERAL |
| 55 | $3.6 \times 10^5$ | $1.1 \times 10^5$ | $1.6 \times 10^4$ | $8.6 \times 10^4$ |
| 55 | $2.9 \times 10^5$ | $9.8 \times 10^4$ | $2.2 \times 10^4$ | $1.1 \times 10^5$ |

TABLE 2

RESULTS OF BIOFILM STUDY USING THE 36 PORT LEGIONELLA RIG

| DAYS AFTER STUD INSERTED | PLANKTONIC COUNT (CFU/ML) | | SESSILE COUNT (CFU/CM$^2$ | |
|---|---|---|---|---|
| | LEGIONELLA | GENERAL BACTERIA | LEGIONELLA | GENERAL BACTERIA |
| 83 | $7.8 \times 10^4$ | $1.72 \times 10^4$ | $2.4 \times 10^4$ | $1.47 \times 10^6$ |
| 83 | $2.0 \times 10^5$ | $1.04 \times 10^5$ | $1.09 \times 10^5$ | $2.45 \times 10^5$ |
| 51 | $4.7 \times 10^3$ | $4.6 \times 10^3$ | $1.6 \times 10^5$ | $2.72 \times 10^5$ |
| 51 | $8.0 \times 10^3$ | $1.56 \times 10^4$ | $8.32 \times 10^4$ | $1.21 \times 10^5$ |
| 76 | $6.0 \times 10^3$ | $1.72 \times 10^4$ | $1.6 \times 10^3$ | $4.96 \times 10^6$ |
| 76 | $8.2 \times 10^3$ | $1.84 \times 10^4$ | $2.17 \times 10^3$ | $2.88 \times 10^6$ |
| 36 | $1.14 \times 10^5$ | $1.76 \times 10^4$ | 96 | $2.24 \times 10^6$ |
| 36 | $1.56 \times 10^5$ | $1.28 \times 10^4$ | 192 | $3.52 \times 10^6$ |
| 43 | $1 \times 10^3$ | $3.6 \times 10^4$ | 0 | $8.96 \times 10^5$ |
| 43 | 220 | $2.62 \times 10^4$ | 9 | $1.88 \times 10^6$ |
| 50 | $6.4 \times 10^4$ | $6.4 \times 10^5$ | $4.16 \times 10^5$ | $1.76 \times 10^7$ |
| 50 | $1.92 \times 10^5$ | $8.8 \times 10^5$ | $4.48 \times 10^5$ | $1.57 \times 10^7$ |
| 58 | $1.16 \times 10^4$ | $5.6 \times 10^5$ | $2.56 \times 10^4$ | $3.1 \times 10^6$ |
| 58 | $3.6 \times 10^3$ | $9.8 \times 10^4$ | $1.6 \times 10^4$ | $4.8 \times 10^6$ |

What is claimed is:

1. A method for monitoring biofilm formation on surfaces in aquatic systems which comprises incorporating in the aquatic system a sampler apparatus comprising a duct which forms a channel for a flow of water and which has at least one port in its walls, a stud having a biofoulable test surface and retaining means comprising a sleeve having a stud-retaining bore, said stud being retained in a first end of said stud-retaining bore, and said sleeve being retained in the port in fixed relationship with respect to the duct so that the test surface is substantially flush with the duct wall and is exposed to water in the channel, said method comprising the steps of:
retaining said stud in the sampler apparatus for an interval for testing;
removing the sleeve from the port;
attaching said stud to a stud removal member to rigidly mount said stud and stud removal member together during removal;
removing said stud from said sleeve in a direction outwardly from the first end of the stud-retaining bore using said stud removal member; and
collecting and analyzing the bacteria from the test surface of said stud.

2. A method according to claim 1 which enables collection of bacteria at more than one time interval for testing the sampler comprising several studs with respective retaining means.

3. A method according to claim 1 in which the duct has several ports in its wall each having an associated stud and respective retaining means.

4. A method according to claim 1 in which the stud comprises a head one side of which forms the test surface and from the opposite side of which extends a stem.

5. A method according to claim 4 in which the stud has a sloping shoulder between the stem and the head.

6. A method according to claim 1 in which the stud is retained in the port by retaining means comprising a sleeve which has a stud retaining bore and which is itself suitable for being retained in the respective port.

7. A method according to claim 1 in which the stud is removed from the sampler apparatus by mounting on the stud removal member comprising a rod, and the mounting means is selected from screw threaded connections, bayonet fixings and push fit connections between the stud and the stud removal member.

8. A method according to claim 1 in which the or each stud comprises a stem and a head, one side of which forms the test surface and from the opposite side of which extends the stem, and in which the stud removal member comprises a rod which has substantially the same diameter as the stud stem.

9. A method according to claim 1 in which the stud removal member is held and/or manipulated during the mounting of the stud by a handle detachably connected to the stud removal member, at the end of the stud removal member distant from the stud mount means.

10. A method according to claim 1 in which the sampler apparatus is connected in parallel with the system being monitored and has an isolating valve at each end.

11. A method according to claim 1 for monitoring biofilm formation on surfaces in aquatic systems in which the stud comprises a head having a test surface and a stem reaching from the head, said method additionally comprising a stud-removal step comprising removing the stud from the sampler apparatus, said stud removal step comprising
positioning over the stem of the stud, a bored sleeve, the test surface of the stud remaining exposed and with the stem in a sliding fit in the bore,
obtaining a removable rigid rod-shaped stud removal member which is slidable through the sleeve bore, and one end of the member has mutually co-operable mounting means with the stud stem,
inserting the member into the sleeve bore so that said mutually operable mounting means of one end of the stud stem are brought into co-operation with each other whilst the stud is received in the sleeve, the stud is thereby mounted on the member for handling before and after removal of the sleeve.

12. A method for monitoring the presence of Legionella bacteria in sessile bacteria in an aquatic system, comprising incorporating in the aquatic system a sampler apparatus comprising a duct which forms a channel for a flow of water and which has at least one port in its walls, a stud having a biofoulable test surface and retaining means comprising a sleeve having a stud-retaining bore, said stud being retained in a first end of said stud-retaining bore, and said sleeve being retained in the port in fixed relationship with respect to the duct so that the test surface is substantially flush with the duct wall and is exposed to water in the channel, said method comprising the steps of:

retaining said stud in the sampler apparatus for an interval for testing;
removing the sleeve from the port;
attaching said stud to a stud removal member to rigidly mount said stud and stud removal member together during removal;
removing said stud from said sleeve in a direction outwardly from the first end of the stud-retaining bore using said stud removal member; and
collecting and analyzing the bacteria from the test surface of said stud.

13. A method according to claim 12 which enables collection of bacteria at more than one time interval for testing the sampler comprising several studs with respective retaining means.

14. A method according to claim 12 in which the duct has several ports in its wall each having an associated stud and respective retaining means.

15. A method according to claim 12 in which the stud comprises a head one side of which forms the test surface and from the opposite side of which extends a stem.

16. A method according to claim 15 in which the stud has a sloping shoulder between the stem and the head.

17. A method according to claim 12 in which the stud is retained in the port by retaining means comprising a sleeve which has a stud retaining bore and which is itself suitable for being retained in the respective port.

18. A method according to claim 12 in which the stud is removed from the sampler apparatus by mounting on the stud removal member comprising a rod, and the mounting means is selected from screw threaded connections, bayonet fixings and push fit connections between the stud and the stud removal member.

19. A method according to claim 12 in which the stud comprises a stem and a head, one side of which forms the test surface and from the opposite side of which extends the stems, and in which the stud removal member comprises a rod which has substantially the same diameter as the said stud stem.

20. A method according to claim 12 in which the stud removal member is held and/or manipulated during the mounting of the stud by a handle detachably connected to the stud removal member, at the end of the stud removal member distant from the stud mount means.

21. A method according to claim 12 in which the sampler apparatus is connected in parallel with the system being monitored and has an isolating valve at each end.

22. A method according to claim 12 for monitoring the presence of Legionella bacteria among sessile bacteria in an aquatic system in which the stud comprises a head having a stem reaching from the head, said method additionally comprising a stud-removal step comprising removing the stud from the sampler apparatus, said stud-removal step comprising positioning over the stem of the stud, a bored sleeve, the test surface of the stud remaining exposed and with the stem in a sliding fit in the bore,
obtaining a removable rigid rod-shaped stud removal member which is slidable through the sleeve bore, and one end of the member has mutually co-operable mounting means with the stud stem,
inserting the member into the sleeve bore so that said mutually operable mounting means of one end of the stud stem are brought into co-operation with each other whilst the stud is received in the sleeve, the stud is thereby mounted on the member for handling before and after removal of the sleeve.

23. A method for monitoring biofilm formation on surfaces in aquatic systems which comprises incorporating in aquatic systems a sampler apparatus comprising a duct which forms a channel for a flow of water and which has at least one port in its walls, a stud having a biofoulable test surface and retaining means comprising a sleeve having a stud-retaining bore, said stud comprising a head having a diameter greater than the diameter of the stud-retaining bore and one side of which forms the test surface and from the opposite side of which extends a stem, said stud being retained in a first end of said stud-retaining bore, and said sleeve being retained in the port in fixed relationship with respect to the duct so that the test surface of the stud is substantially flush with the duct wall and is exposed to water in the channel, said method comprising the steps of:

retaining said stud in the sampler apparatus for an interval for testing;
removing the sleeve from the port;
attaching said stud to a stud removal member to rigidly mount said stud and stud removal member together during removal;
removing said stud from said first end of said sleeve in a direction outwardly from the first end of the stud-retaining bore using said stud removal member; and
collecting and analyzing the bacteria from the test surface of said stud.

24. A method according to claim 23 in which the stud removal member comprises a rod which has substantially the same diameter as the said stud stem.

25. A method according to claim 23 in which the stud removal member is held or manipulated during the mounting of the stud or both by a handle detachable connected to the stud removal member at the end of the stud removal member distant from the stud mount means.

26. A method according to claim 23 in which the stud removal member comprises a rod which has substantially the same diameter as said stud stem and in which the stud removal member is held or manipulated during the mounting of the stud or both by a handle detachably connected to the stud removal member at the end of the stud removal member distant from the stud mount means.

27. A method for monitoring biofilm formation on surfaces in aquatic system which comprises incorporating in aquatic systems a sampler apparatus comprising a duct which forms a channel for a flow of water and which has at least one port in its wall, a stud having a biofoulable test surface and retaining means comprising a sleeve having a stud retaining bore, said stud comprising a head, one side of which forms the test surface and from the opposite side of which extends a stem, said stud having a sloping shoulder between the head and the stem, the surface area of the head being greater than the cross sectional area of the stem, and said stud being retained in a first end of said stud-retaining ore, and said sleeve being retained in the port in fixed relationship with respect to the duct so that the test surface of the stud is substantially flush with the duct wall and is exposed to water in the channel, said method comprising the steps of:

retaining the stud in the sampler apparatus for an interval for testing;

removing the sleeve from the port;

attaching said stud to a stud removal member to rigidly mount said stud and stud removal member together during removal;

removing said stud from said first end of said sleeve in a direction outwardly from the first end of the stud-retaining bore using a stud removal member;

collecting and analyzing the bacteria from the test surface of said stud.

28. A method according to claim 27 in which the stud removal member comprises a rod which has substantially the same diameter as said stud stem and in which the stud removal member is held or manipulated during the mounting of the stud or both by a handle detachably connected to the stud removal member at the end of the stud removal member distant from the stud mount means.

* * * * *